(12) United States Patent
Crank et al.

(10) Patent No.: US 6,616,626 B2
(45) Date of Patent: Sep. 9, 2003

(54) INFUSION DEVICES AND METHOD

(75) Inventors: Justin Crank, Minneapolis, MN (US); Scott Larson, St. Louis Park, MN (US); Timothy J. Mickley, Elk River, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/747,157

(22) Filed: Dec. 21, 2000

(65) Prior Publication Data

US 2002/0082546 A1 Jun. 27, 2002

(51) Int. Cl.[7] ............................................. A61M 31/00
(52) U.S. Cl. ......................................................... 604/48
(58) Field of Search .......................... 604/48, 117, 160, 604/164.12, 165.02, 166.01

(56) References Cited

U.S. PATENT DOCUMENTS

| 4,279,252 A | * | 7/1981 | Martin ........................ 378/163 |
| 4,434,822 A | * | 3/1984 | Bellamy et al. ............. 141/114 |

(List continued on next page.)

FOREIGN PATENT DOCUMENTS

| DE | 296 09 350 U 1 | 10/1996 |
| DE | 195 37 084 A 1 | 4/1997 |
| WO | WO 96/35469 | 11/1996 |
| WO | WO 96/39963 | 12/1996 |
| WO | WO 97/18768 | 5/1997 |
| WO | WO 97/29803 | 8/1997 |
| WO | WO 97/32551 | 9/1997 |
| WO | WO 97/44071 | 11/1997 |
| WO | WO 98/05307 | 2/1998 |
| WO | WO 98/16157 | 4/1998 |
| WO | WO 98/17186 | 4/1998 |
| WO | WO 99/22655 | 5/1999 |
| WO | WO 00/15146 | 3/2000 |
| WO | WO 00/16704 | 3/2000 |

OTHER PUBLICATIONS

Mirhoseini et al., Abstract entitled "Transventricular Revascularization by Laser", *Lasers in Surgery and Medicine*, 2(2), 1982, 1 page.
Gal et al., Abstract entitled "Analysis of Photoproducts Free Radicals and Particulate Debris Generated...", *Lasers in Surgery and Medicine*, 11(2) 1991, 1 page.

(List continued on next page.)

*Primary Examiner*—Henry C. Yuen
*Assistant Examiner*—Hyder Ali
(74) *Attorney, Agent, or Firm*—Kenyon & Kenyon

(57) ABSTRACT

Devices and methods for performing improved percutaneous myocardial revascularization (PMR) procedures. One device includes a preassembled PMR drug delivery catheter and a drug neutralizing vial. The vial assembly allows prepping the PMR catheter by flushing drug through distal needle, and into a vial cavity where the drug is neutralized by a neutralizing agent. One set of devices includes needles having protrusions secured to the distal regions of drug delivery tubes. One needle has outward protruding barbs engaging the inner tube wall while another needle has outward threads which can screw into the tube inner wall. Radiopaque marker bands are also included in the present invention which are asymmetrically distributed on the catheter shaft, allowing a treating physician to determine under fluoroscopy whether the catheter distal region is pointed away or toward the treating physician, as well as determining whether the catheter distal region is rotated toward or away from the treating physician. PMR devices include catheters having dual injection needles, for both injecting a drug into the heart wall and a radiopaque contrast media to mark the already treated sites. One PMR injection device has multiple stops for allowing controlled, variable needle depth penetration with a single distal needle tip.

19 Claims, 6 Drawing Sheets

U.S. PATENT DOCUMENTS

| | | | |
|---|---|---|---|
| 4,760,131 A | 7/1988 | Sundsmo et al. | 530/356 |
| 4,790,311 A | 12/1988 | Ruiz | 128/303.1 |
| 4,896,671 A | 1/1990 | Cunningham et al. | 128/642 |
| 5,047,026 A | 9/1991 | Rydell | 606/48 |
| 5,093,877 A | 3/1992 | Aita et al. | 385/34 |
| 5,261,889 A | 11/1993 | Laine et al. | 604/164 |
| 5,287,861 A | 2/1994 | Wilk | 128/898 |
| 5,358,485 A | 10/1994 | Vance et al. | 604/22 |
| 5,364,393 A | 11/1994 | Auth et al. | 606/34 |
| 5,370,675 A | 12/1994 | Edwards et al. | 607/101 |
| 5,380,316 A | 1/1995 | Aita et al. | 606/7 |
| 5,389,096 A | 2/1995 | Aita et al. | 606/15 |
| 5,403,311 A | 4/1995 | Abele et al. | 606/49 |
| 5,429,256 A | 7/1995 | Kestenbaum | |
| 5,431,649 A | 7/1995 | Mulier et al. | 606/41 |
| 5,522,815 A | 6/1996 | Durgin, Jr. et al. | 606/50 |
| 5,551,427 A | 9/1996 | Altman | 128/642 |
| 5,569,462 A | 10/1996 | Martinson et al. | 424/424 |
| 5,591,159 A | 1/1997 | Taheri | 606/15 |
| 5,593,405 A | 1/1997 | Osypka | 606/15 |
| 5,607,405 A | 3/1997 | Decker et al. | 604/264 |
| 5,620,414 A | 4/1997 | Campbell, Jr. | 604/22 |
| 5,672,174 A | 9/1997 | Gough et al. | 606/41 |
| 5,674,192 A * | 10/1997 | Sahatjian et al. | 604/28 |
| 5,681,308 A | 10/1997 | Edwards et al. | 606/41 |
| 5,683,366 A | 11/1997 | Eggers et al. | 604/114 |
| 5,697,882 A | 12/1997 | Eggers et al. | 604/114 |
| 5,700,259 A | 12/1997 | Negus et al. | 606/14 |
| 5,713,894 A | 2/1998 | Murphy-Chutorian et al. | 606/15 |
| 5,725,521 A | 3/1998 | Mueller | 606/7 |
| 5,725,523 A | 3/1998 | Mueller | 606/15 |
| 5,810,836 A | 9/1998 | Hussein et al. | 606/108 |
| 5,871,495 A | 2/1999 | Mueller | 606/185 |
| 6,042,581 A | 3/2000 | Ryan et al. | 606/45 |
| 6,045,565 A | 4/2000 | Ellis et al. | 606/167 |
| 6,053,911 A | 4/2000 | Ryan et al. | 606/33 |
| 6,053,924 A | 4/2000 | Hussein | 606/108 |
| 6,056,742 A | 5/2000 | Murphy-Chutorian et al. | 606/11 |
| 6,056,743 A | 5/2000 | Ellis et al. | 606/15 |
| 6,217,554 B1 | 4/2001 | Green | |
| 6,285,903 B1 * | 9/2001 | Rosenthal et al. | 600/424 |
| 6,464,693 B1 * | 10/2002 | Andrews et al. | 606/15 |

OTHER PUBLICATIONS

Isner, J., Abstract entitled "Right Ventricular Myocardial Infarction", *Jama*, v259, n5, Feb. 5, 1988, 12 pages.

Pickering et al., Abstract entitled "Proliferative Activity in Perpheral and Coronary Atherosclerotic Plaque....", *J. Clin. Invest.*, ISSN 0021-9738, Apr. 1993, 1 page.

Vineberg et al., "Creation of Intramyocardinal Pathways to Channel Oxygenated Blood Between Ventricular Arteriolar Zones", *Canad. Med. Ass. J.*, vol. 96, Feb. 4, 1967, 3 pages.

Vineberg, A., "Results of 14 Years' Experience in the Surgical Treatment of Human Coronary Artery Insufficiency", *Canad. Med. Ass. J.*, vol. 92, Feb. 13, 1965, 8 pages.

Vineberg et al., "The Ivalon Sponge Procedure for Myocardial Revascularization", *Surgery*, vol. 47, No. 2, Feb. 1960, pp. 268–289.

Vineberg et al., "Treatment of Acute Myocardial Infarction by Endocardial Resection", *Surgery*, vol. 57, No. 6, Jun. 1965, pp. 832–835.

Walter et al., "Treatment of Acute Myocardial Infarction by Transmural Blood Suply from the Ventricular Cavity", *European Surgical Research*, 3:130–138 (1971).

Khazei et al., "Myocardial Canalization", *The Annals of Thoracic Surgery*, vol. 6, No. 2, Aug. 1968, pp. 163–171.

Hershey et al., "Transmyocardial Puncture Revascularization", *Geriatrics*, Mar. 1969, pp. 101–108.

Press Release dated Oct. 21, 1996, "Doctor's Demonstrate Proof of Blood Flow Through Open TMR Channels Created with PLC Systems...", 1 page.

Press/News Release dated Oct. 10, 1996, "Texas Fieart Institute Presents Study Comparing the Use of $CO_2$...", 1 page.

Goldman et al., "Nonoperative Portacaval Shunt in Swine", *Investigative Radiology*, vol. 25, No. 5, May 1990, 5 pages.

Schumacher et al., "Induction of Neoangiogenesis in Ischemic Myocardium by Human Growth Factors", *Clinical Investigation and Reports*, Dec. 1, 1997, 6 pages.

Article entitled "Gene therapy improves leg circulation—next step heart?", $70^{th}$ Scientific Sessions, published on or before Nov. 2, 1998, 2 pages.

Winslow, R., "Genetic Techniques Succeed in Treating Patients with Obstructed Blood Vessels", *The Wall Street Journal*, published on or before Nov, 2, 1998, 2 pages.

Kolata, G., "Gene Therapy Gives Blood a Path Around Leg Blockages, Researchers Say", *The New York Times*, Nov. 10, 1997, 2 pages.

Mack et al., "Cardiopulmonary Support and Physiology", *The Journal of Thoracic and Cardiovascular Surgery*, vol. 115, No. 1, Jan., 1998, 10 pages.

Annex Form PCT/ISA/206, Communication Relating to the Results of the Partial International Search for PCT/US01/48839.

* cited by examiner

Fig. 5D
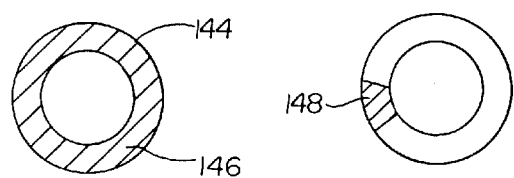
Fig. 5E
Fig. 6D
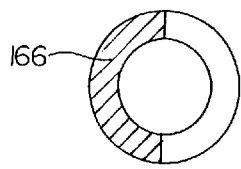
Fig. 6E
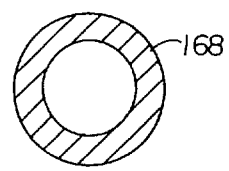
Fig. 7
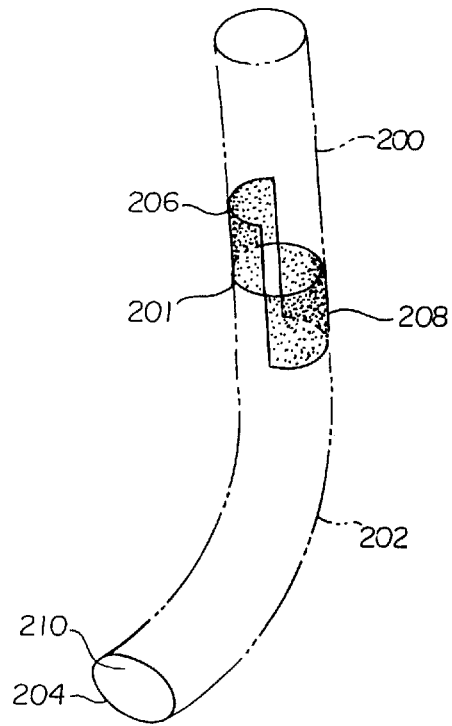

INFUSION DEVICES AND METHOD

FIELD OF THE INVENTION

The present invention is related generally to medical devices. More specifically, the present invention is related to devices associated with delivery of genes or therapeutic substances.

BACKGROUND OF THE INVENTION

A number of techniques are available for treating heart disease and diseases of other organs percutaneously. Examples of such techniques include delivery of genes and therapeutic substances, including the delivery of genes and therapeutic substances for percutaneous myocardial revascularization (PMR). This procedure is performed to increase blood perfusion through the myocardium of a patient. For example, in some patients, the number of lesions in coronary vessels is so great or the location so remote in the patient vasculature that restoring blood flow to the heart muscle is difficult. Percutaneous myocardial revascularization (PMR) has been developed as an alternative to techniques which are directed at bypassing or removing lesions. PMR is performed by boring holes directly into the myocardium of the heart. Positive results have been demonstrated in some human patients receiving PMR treatments. These results are believed to be caused in part by blood flowing from within a heart chamber through patent holes formed by PMR to the myocardial tissue. Suitable PMR holes have been proposed to be burned by laser, cut by mechanical means, and burned by radio frequency devices. Increased blood flow to the myocardium is also believed to be caused in part by the healing response to wound formation, specifically, the formation of new blood vessels in response to the newly created wound.

Several aspects of PMR procedures could be improved upon. One area for improvement is in the preparation of PMR injection catheters for use by the treating physician. In particular, at present, the PMR device maybe flushed with a drug to prime the distal needle by flushing the drug through the needle and into a container. This preparation can be awkward and may leave a container of biologically active material which may require further processing. Another aspect which may be further optimized lies in the attachment of the needle to the distal region of the PMR catheter tube. In particular, forces may act upon the needle during both the advancement and retraction of the needle within the heart wall, urging the needle undesirably both into and out of the tube. Improved methods of securing the needle to the tube would be desirable.

During a PMR treatment, a physician may be attempting to treat a three-dimensional space using a catheter having a distal bend. In particular, the physician may be attempting to treat the heart chamber side, anterior, and posterior wall regions. This may presently be difficult to visualize under fluoroscopy as current marking systems for shafts may make interpretation of the catheter distal region orientation somewhat ambiguous. The heart chamber wall thickness can vary depending on the chamber and wall region being treated. In particular, the left ventricle wall is thinner in the posterior region relative to the anterior region. Improved devices for variable depth, yet controlled penetration of the heart walls, would be advantageous. As multiple sites of the heart chamber wall are penetrated, a system for tracking the treated versus untreated regions would also be desirable.

SUMMARY OF THE INVENTION

The present invention includes improved devices and methods for performing PMR procedures. One device allows for improved preparation of PMR catheters used to inject a drug or therapeutic substance into the heart wall. One such device includes a PMR device distal region or hood disposed within the neck of a vial for receiving the drug. The vial can be used to receive the drug while the drug is being flushed through the PMR device and needle to prepare the PMR device for use. One vial has a neck and shoulder region for receiving and retaining the distal region of a PMR injection device. A no-leak gasket defines one wall of an inner cavity within one such vial.

The vial is preferably formed of a transparent or translucent material for observing the injection of the drug into the vial. In one embodiment, the vial cavity includes a drug-neutralizing agent. The agent allows the drug to be neutralized after receiving the drug. A neutralizing agent can provide improved safety, should the integrity of the vial be breached. The drug-neutralizing vial allows a biologically active drug to be flushed through the catheter with the vial being disposed of in a normal waste stream such as a wastebasket, rather than requiring special handling.

One set of devices provides improved needle attachment to drug delivery tubes. One improved drug delivery tube has an outer tube defining a lumen therein. A needle may be disposed within the distal end of the tube. The needle can have a distal, sharp tube region for insertion into the heart wall, as a well as a wider, more proximal region having outward protrusions for engaging or biting into the drug delivery tube inner wall. One device has a wide flange for abutting the drug delivery tube distal end, thereby limiting the proximal travel of the needle into the drug delivery tube lumen. One drug delivery tube also has a bonding hole which can be used to inject an adhesive to further secure the needle within the drug delivery tube distal region. The improved securing of the needle to the drug delivery tube can act to prevent the needle from being distally pulled from the tube.

During insertion of the needle into the heart wall, forces can act to urge the needle into the tube. Upon retraction of the needle from the heart wall, forces may act to pull the needle distally from the tube. Both the outward protrusions, the flange, and the added adhesive can act to better secure the needle to the drug delivery tube. One embodiment includes outward barbs biting into the drug delivery tube, while another embodiment uses a series of helically disposed screw threads to engage the tube wall. A preferred embodiment uses outward protruding elements which engage the inner wall, while another embodiment uses inwardly protruding elements engaging the outer wall of the tube distal region.

Another aspect of the invention provides improved visualization of the catheter shaft orientation under fluoroscopy. One embodiment utilizes asymmetrically disposed radiopaque markers on the shaft distal region to enable the treating physician to determine whether the catheter distal region is pointed at right angles to the treating physician or is pointed toward or away from the treating physician. One embodiment has the radiopaque marker being asymmetrically distributed with respect to a plane bisecting a longitudinal axis of the catheter tube distal region. Another embodiment further includes the radiopaque marker being asymmetrically distributed with respect to length over the catheter distal region. One marker includes an annular ring portion and a straight leg portion lying along the length of one side of the tube. Yet another embodiment includes an annular shell or ring portion and an annular arc leg portion extending along a length from the annular shell or ring portion. The radiopaque markers may be disposed on either the proximal or the distal side of any bend in the catheter shaft. A preferred use of the radiopaque marker band is on a guide catheter used to guide a PMR therapeutic tip to the heart wall.

In yet another aspect of the invention, radiopaque marker segments are asymmetrically distributed such that the rotation of the tube relative to the treating physician may be determined under fluoroscopy. One embodiment uses opposing annular shells on opposing sides of a tube where the annular shells are shifted longitudinally relative to each other. The asymmetrically disposed shells are thus asymmetric both with respect to a plane bisecting a longitudinal central access and with respect to a plane transversely bisecting a catheter shaft.

In still another aspect of the invention, marker bands are provided a distance apart which approximates the desired inter-treatment site spacing along the heart wall. A method can be performed using this aspect of the invention, whereby a therapeutic substance is delivered at treatment sites which are observed under fluoroscopy to be spaced apart approximately the distance between marker bands. Any distortion or magnification of the distances between marker bands will approximately be matched by distortions between treatment sites.

The present invention also includes a PMR device for allowing precise, variable depth needle penetration of the heart wall. One device includes at least one inner stop affixed to a rotatable inner needle. The device also can have one or more stops disposed inwardly from an outer tube, the outer tube having the inner needle rotatably disposed within. The inner needle can be longitudinally advanced until the inner stop abuts an outer stop, thereby inhibiting further distal movement of the inner needle. If greater penetration is desired, the inner shaft can be rotated, thereby swinging the inner stop clear of the first encountered outer stop, allowing the inner stop to proceed further distally until a subsequent outer stop is encountered. This aspect of the invention allows a single device to be used, yet provides multiple, preset, precise penetration depths. This may be of particular use where the thickness of the heart wall varies over different regions of the heart chamber wall.

Yet another aspect of the invention provides for injection of drug and contrast media into the heart wall. Injection of contrast media near the injection site of a drug allows the treating physician to visualize under fluoroscopy which areas of the heart wall have been treated and which have not yet been treated. One device provides a contrast media injection needle disposed side-by-side with a drug delivery needle. One embodiment allows the two side-by-side needles to be retracted and advanced together. The needles can be distally straight, arcuate, or one arcuate and one straight. Another embodiment provides a drug and contrast media injection device having a pair of needles, one being coaxially disposed within the other. The innermost needle can be used to inject drug deep into the heart tissue, while the more outer, coaxially disposed needle may be used to inject contrast media to the heart wall, thereby marking the site of treatment. One embodiment utilizes a sharp, cutting end to inject contrast media. Another embodiment uses a less sharp, less cutting end, for injecting a contrast media into the heart wall tissue using pressure, rather than cutting.

BRIEF DESCRIPTION OF THE DRAWINGS

FIGS. 5D–5E are transverse, cross-sectional views taken through the catheter of FIGS. 5A–5C;

FIGS. 6D–6E are transverse, cross-sectional views taken through the catheter of FIGS. 6A–6C;

FIG. 7 is a perspective view of a catheter shaft having an asymmetric, radiopaque marker disposed proximal of a bend;

DETAILED DESCRIPTION OF THE PREFERRED EMBODIMENTS

Figure 1:
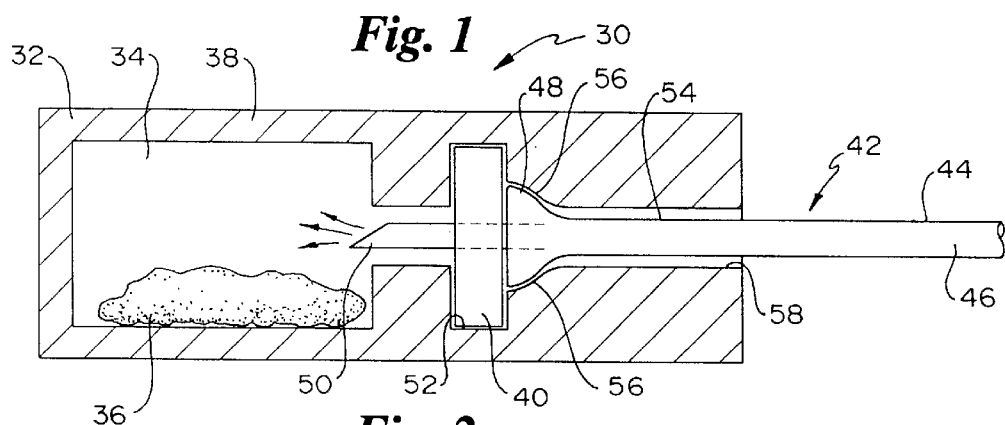
FIG. 1 is a fragmentary, side, cutaway view of a myocardial revascularization preparation system including a drug neutralizing vial and a myocardial revascularization drug delivery catheter in the process of being prepared for use by flushing a drug through the injection needle into the drug-neutralizing vial.

FIG. 1 illustrates a myocardial revascularization drug delivery preparation assembly 30 including a drug receiving vial 32 and a drug delivery catheter 42 inserted into vial 32. Drug delivery catheter 42 includes a tube 44 having a lumen 46 therethrough. Catheter 42 includes a distal portion 54 having an injection device or needle 50 in fluid communication with lumen 46. Catheter 42 further includes a distal hood 48, illustrated in an expanded state. Drug injection needle 50 is illustrated penetrating through a self-sealing, no-leak gasket 40. Gasket 40 can be disposed within vial 32 in an annular seat 52, as shown.

Drug receiving vial 32 includes a wall 38, which is preferably formed of a transparent or translucent material, allowing both an expelled drug and catheter needle to be viewed through the vial wall. Vial 32 includes a cavity 34 having a drug-neutralizing agent 36 disposed within cavity 34. Vial 32 includes a neck region 58 for receiving catheter distal portion 54. In one embodiment, vial 32 further includes a shoulder or contour region 56 for engaging catheter distal hood 48. In some embodiments, vial shoulder 56 and catheter hood 48 are cooperatively sized such that shoulder 56 engages hood 48 even when hood 48 is in a non-expanded state. Hood 48 is preferably sufficiently compliant so as to allow retraction of hood 48 through vial neck region 58 after preparing the catheter. Vial shoulder 56 can also flex to contain hood 48.

In use, drug delivery catheter preparing system 30 can be provided substantially as illustrated in FIG. 1. Catheter 42 can be provided either separate from, or already engaged within, vial neck region 58. When catheter 42 is to be prepared, catheter 42 distal portion 54 can be inserted into vial neck region 58, if not already so disposed. Catheter 42 can be further advanced, forcing needle 50 through gasket 40, and into cavity 34. With needle 50 inserted through gasket 40, the drug to be delivered can be flushed through needle 50 into cavity 34, preferably mixing with a neutralizing agent. In this way, the drug to be delivered can be loaded into catheter 42, preparing the catheter for use. The excess drug can be contained within cavity 34, which may be desirable where the drug is potentially harmful or must be isolated for other reasons. Catheter 42 can be retracted from vial 32 when needed. Gasket 40 is preferably formed of a self-sealing material, such that a seal is re-formed after needle 50 is withdrawn. In embodiments having a drug-neutralizing agent, the contents of the vial will be harmless, even if the vial integrity is compromised. After preparing, vial 32 can be disposed of in a proper manner. In some embodiments, vial 32, containing either a harmless or a neutralized drug, may be disposed of in a wastebasket, with no special handling required.

Catheter 42 can be used to inject various drugs or other therapeutic substances into the myocardium. Examples of therapeutic substances include small molecular drugs, proteins, genes and cells which could promote angiogenesis, protect tissues (i.e., cardiac protection), or promote tissue regeneration. Vascular Endothelial Growth Factor (VEGF) and Fibroblast Growth Factors (FGFs) are believed suitable for use with the present invention. Carriers for the therapeutic agents of the present invention can include polymers, angiopoietins, biodegradable and biostable hydrogels, and dissoluble polymers. Adhesives suitable for binding the present invention include fibrin glues and cyanoacrylates which may also be included with the therapeutic substance to improve the desired response. Drug injection catheters referred to in the remainder of the present patent application, and drugs similarly referenced, may include the injection and use of the aforementioned therapeutic substances.

Catheter 42, as well as subsequently referenced drug injection catheters or myocardial revascularization catheters, can include catheters such as those described in co-pending U.S. patent application Ser. No. 09/271,045, filed Mar. 17, 1999, entitled TRANSMYOCARDIAL REVASCULARIZATION CATHETER AND ASSEMBLY; and U.S. patent application Ser. No. 09/184,220, filed Nov. 2, 1998, entitled PERCUTANEOUS MYOCARDIAL REVASCULARIZATION GROWTH FACTOR MEDIUMS AND METHOD, herein incorporated by reference. In particular, guide catheters described according to the present invention may be used to guide these previously referenced devices, and others, to target sites in the myocardium.

Figure 2:
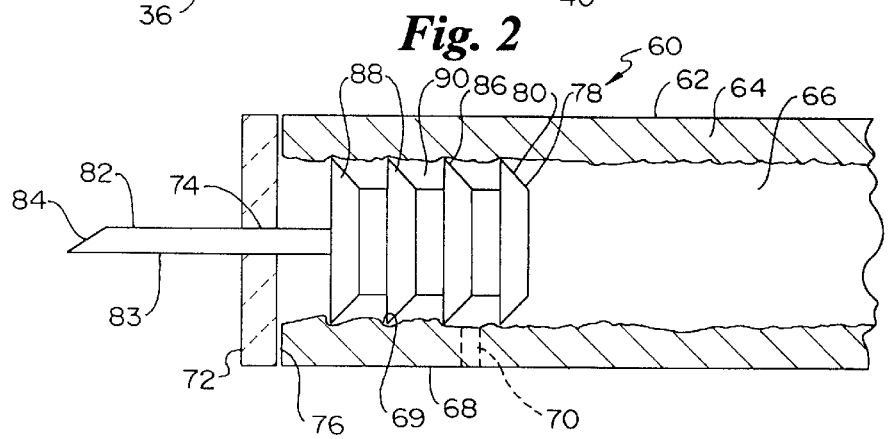
FIG. 2 is a fragmentary, longitudinal, cross-sectional view of a drug delivery catheter distal portion having a needle disposed within a tube, the needle having barbs for engaging the tube inner wall to improve needle retention.

FIG. 2 illustrates the distal portion of a drug delivery catheter 60 which, in a preferred use, can be used for a procedure such as myocardial revascularization. Drug delivery catheter 60 includes a tube 62 having a wall 64 defining a drug delivery lumen 66 within. Catheter 60 has a distal region 68, terminating in a distal end 76. Disposed within catheter tube 62 is a drug delivery needle 78, including generally a wider, proximal portion 80, and a narrower, distal portion 82. Distal portion 82 includes an elongate tube 83 terminating in a sharp end 84. Needle wide proximal portion 80, in the embodiment illustrated, includes a plurality of wider protrusions 88 spaced apart from each other by a plurality of narrower regions 90. Protrusions 88, in a preferred embodiment, include sharp tips or barbs 86 for engaging and gripping tube wall 64.

As can be seen in FIG. 2, outward protrusions or barbs 86 may form a plurality of deformations 69 where the barbs dig into tube wall 64. In a preferred embodiment, barbs 86 have at least a slight inclination toward the distal direction, such that retraction of needle 78 from tube 62 is more difficult than insertion of needle 78 into tube 62. In a preferred embodiment, drug delivery catheter 60 includes a distal flange 72 which can serve to limit travel of needle 78 into drug lumen 66. In the embodiment illustrated, flange 72 abuts tube distal end 76 and has a hole 74 therethrough for receiving needle distal tube portion 83. In one embodiment, tube 62 includes a bonding hole 70 through tube wall 64 for receiving adhesive. Adhesive can be injected through hole 70 for improving the adherence of needle wide portion 80 to tube distal region 68.

In one use, drug delivery catheter 60 can be advanced through the vasculature and into a heart chamber wall. After injection of a drug through drug lumen 66, drug delivery catheter 60 can be retracted, thereby retracting needle distal end 84. In a situation where the heart wall grips needle distal tube portion 83, barbs or protrusions 86 can serve to resist the distally directed force attempting to retain needle 78.

Figure 3:
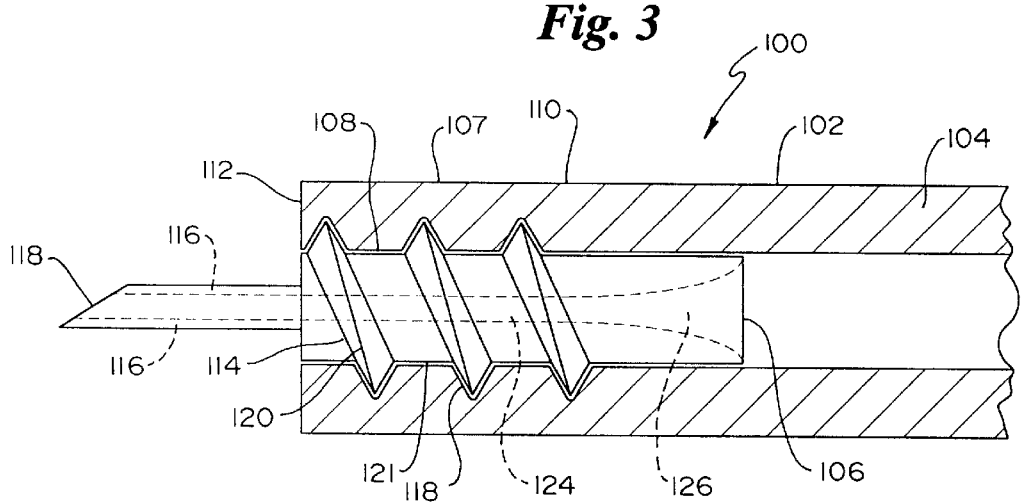
FIG. 3 is a fragmentary, longitudinal, cross-sectional view of a drug delivery catheter distal portion having a needle disposed within a tube, the needle having threads for engaging the tube inner wall to improve needle retention.

Another drug delivery catheter 100 is illustrated in FIG. 3, having a needle 114 disposed within a tube 102. Tube 102 includes a tube wall 104 having an inner surface 108 and an outer surface 107. Tube 102 includes a distal region 110, a distal end 112, and a lumen 106 disposed therethrough. Needle 114 includes a distal tip region 116 ending distally in a sharp distal end 118. Needle 114 also includes a proximal needle portion 118 including a plurality of threads 120 which are spaced apart and have narrower regions 121 disposed between threads 120. Needle 114 includes a needle lumen 124 extending through needle 114 and having a proximal throat region 126. Throat 126 can improve the flow characteristics of fluid through the needle. Needle threads 120 may be seen to engage or bite into tube wall 104. In the embodiment illustrated, threads 120 are disposed on the outside of needle 114, and engage inner surface 108 of tube wall 104. In another embodiment, not requiring illustration, the proximal portion of the needle extends over tube 104. In this embodiment, threads are disposed inward within the needle lumen and engage tube outer surface 107, rather than the inner surface. Needle 114 can be secured to tube 102 by advancing needle 114 into tube lumen 106 and rotating 114, thereby screwing needle 114 into tube lumen 106. Threads 120 thus secure needle 114 to tube 102 and resist the distally directed forces attempting to urge needle 114 out of tube 102.

Figure 4A:
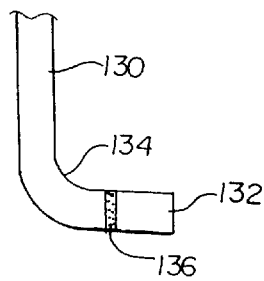
FIGS. 4A–4C are perspective views of a prior art catheter shaft having an annular radiopaque band.
Figure 4B:
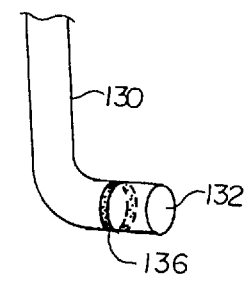
Figure 4C:
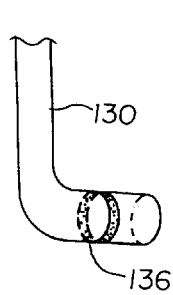

FIGS. 4A through 4C illustrate a prior art catheter shaft 130 having a bend 134 and extending to a distal end 132. Catheter shaft 130 has an annular band 136 which includes a radiopaque material. FIG. 4A is a side view, viewing catheter shaft 130 from an angle of about ninety degrees (90°) away from a straight-on end view looking directly along the central longitudinal axis. FIG. 4B illustrates catheter 130 viewed from an angle of less than ninety degrees (90°) off the center longitudinal axis. FIG. 4B illustrates catheter shaft 130 where distal end 132 is pointed more toward the viewer than away. FIG. 4C illustrates catheter shaft 130 being pointed more away from than toward the viewer. FIGS. 4B and 4C illustrate that annular radiopaque band 136 looks somewhat elliptical, and looks about the same, whether viewed from the front or the back. Annular band 136 thus looks the same when catheter shaft distal end 132 is pointed toward or away from the viewer. Annular radiopaque band 136 gives no indication under fluoroscopy of the direction the catheter shaft distal end is pointed. This is a less than optimal attribute of annular radiopaque band 136, when used in an application such as myocardial revascularization, where the catheter shaft may be rotated and translated in all directions.

Figure 5A:
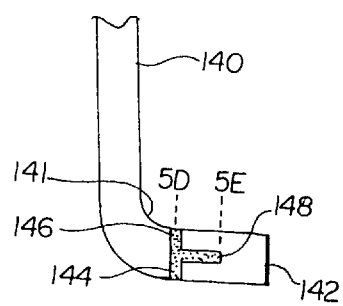
FIGS. 5A–5C are perspective views of a catheter shaft having an asymmetric radiopaque marker.
Figure 5B:
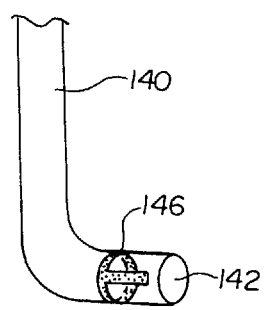
Figure 5C:
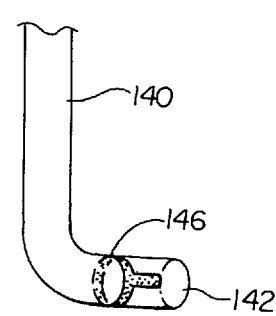

FIGS. 5A through 5E illustrate a catheter shaft 140 having an asymmetric radiopaque marker. Catheter shaft 140 includes a bend 141 disposed proximal of a distal end 142. Catheter 140 includes an asymmetric radiopaque marker 144 including a first, annular or ring portion 146 extending radially about the catheter and disposed transversely to the catheter longitudinal axis, and a second, straight portion 148, extending along one side of shaft 140 toward distal end 142. FIG. 5A illustrates a side view of catheter shaft 140. The view of FIG. 5A is taken from about ninety degrees (90°) away from a straight-on end view, a view which would look directly along the central longitudinal axis. FIG. 5B illustrates a view of catheter shaft 140 with shaft distal end 142 pointed more toward the viewer than away. FIG. 5C illustrates catheter shaft 140 having distal end 142 pointed more away from the viewer than toward the viewer. As can be seen from inspection of FIGS. 5B and 5C, marker 144 appears differently when the catheter distal end is pointed away from the viewer compared to pointing toward the viewer. The asymmetric marker band 146 thus provides an indication under fluoroscopy of whether the catheter is pointed away from, or toward the viewer.

FIG. 5D illustrates the asymmetric nature of radiopaque marker 144. FIG. 5D, taken through annular ring portion 146, shows a more proximal slice through catheter shaft 140. FIG. 5E, taken through a more distal portion of catheter 140, illustrates marker 144 having straight leg portion 148 only on one side. It may be seen from FIGS. 5A through 5E that a plane bisecting the central longitudinal axis of catheter shaft 140, will have differing, asymmetrical portions of radiopaque marker on either side of the bisecting plane. In particular, the markers on either side of the bisecting plane are not mirror images of each other. It may also be seen that marker 144, when compared proximal end to distal end, is asymmetric along its length. In particular, radiopaque marker 144 does not have a distal portion which is a mirror image of its more proximal portion.

Figure 6A:
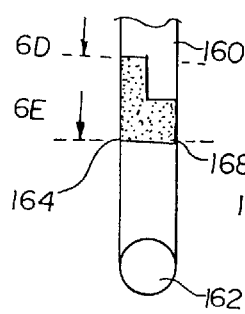
FIGS. 6A–6C are perspective views of a catheter having an asymmetric radiopaque marker.
Figure 6B:
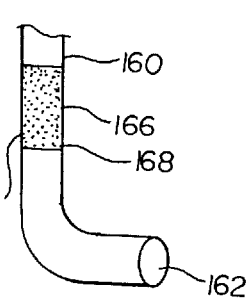
Figure 6C:
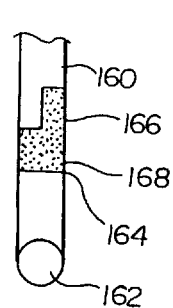

FIG. 6A illustrates a catheter 160 having a radiopaque marker 164 which is asymmetric and includes a first, annular arc shell portion 166, and a second, annular ring portion 168. In FIG. 6A, it may be seen that a plane bisecting the central longitudinal axis of catheter 160 would have an asymmetry with respect to the marker about the bisecting plane. In particular, the right and left halves of catheter 160 are not mirror images of each other. In FIG. 6A, catheter distal end 160 is pointed directly at the viewer. In FIG. 6B, catheter 160 is directed such that catheter distal end 162 is pointed ninety degrees (90°) away from the viewer, directly to the side. In FIG. 6C, catheter 160 is pointed one hundred eighty degrees (180°) away from the viewer, toward the back. Comparison of FIGS. 6A through 6C illustrates that marker 164 appears differently depending whether catheter distal end 162 is pointed toward the viewer, to the side of the viewer, or away from the viewer. FIG. 6D shows a transverse cross-section taken through radiopaque annular shell 166. Annular arc shell 166 extends along the length of the catheter and substantially parallel to the central longitudinal axis, similar in some respects to straight segment 140 of FIGS. 5A through 5E, but wider. FIG. 6E shows a transverse cross-section taken through marker 164 through annular ring 168. The asymmetry about the bisecting plane may be seen in FIGS. 6D and 6E, as well. Radiopaque marker 164 may also be seen to be asymmetric about a transverse bisecting plane. In particular, the top half of marker 164 in FIG. 6A is not the mirror image of a bottom half of marker 164 in FIG. 6A.

In comparing FIGS. 5A through 5C and 6A through 6C, it may be seen that both embodiments, when viewed from an angle orthogonal to a plane containing the shaft on either side of the bend, have an asymmetric marker having two portions. The first portion lies substantially within a plane transverse to the center longitudinal axis. The second portion lies substantially within a plane that contains the center longitudinal axis. One embodiment has the marker disposed proximal of the bend, while the other embodiment has the marker disposed distal of the bend. One embodiment indicates shaft rotation proximal of the bend directly and infers the orientation of the segment distal of the bend. Another embodiment indicates shaft rotation distal of the bend directly and infers the orientation of the segment proximal of the bend. The other embodiment, not requiring illustration, has both the markers of FIGS. 5A through 5C and 6A through 6C on the same shaft.

FIG. 7 illustrates a catheter shaft 200 having a radiopaque marker 201 including a first portion 206 and a second portion 208. Catheter 200 has a bend 202 and a distal end 204. In the embodiment illustrated, catheter 200 has a lumen 210 extending therethrough. As can be seen from inspection of FIG. 7, a plane bisecting the center longitudinal axis through catheter shaft 200 would bisect radiopaque marker 201 into two halves 206 and 208, with the halves being asymmetric relative to the bisecting plane. In particular, first marker portion 206 and second marker portion 208 are not mirror images of each other with respect to a bisecting plane sending through the central axis. Radiopaque marker 201 is also not symmetrical with respect to a transverse bisecting plane. The asymmetry causes marker 201 to appear differently depending on the rotation of the tube with respect to a viewer. In particular, marker 201 will appear differently under fluoroscopy depending on the degree to which the catheter is rotated about its central, longitudinal axis proximal of bend 202.

Figure 8A:
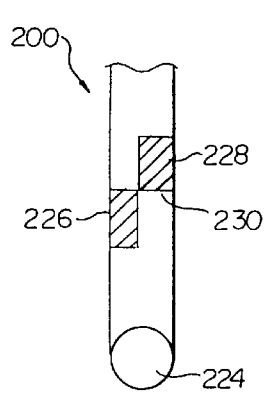
FIGS. 8A–8H are plan views of a catheter shaft having an asymmetric radiopaque marker in varying degrees of rotation.
Figure 8B:
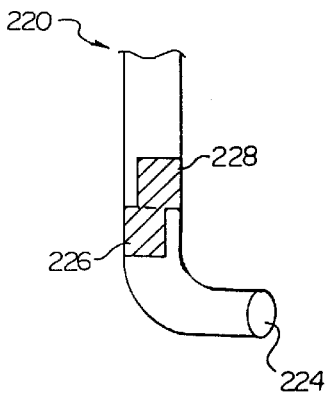
Figure 8C:
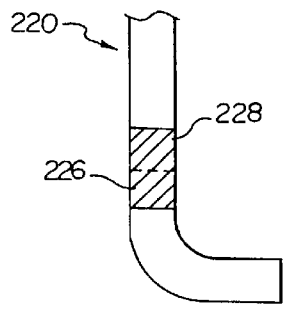
Figure 8D:
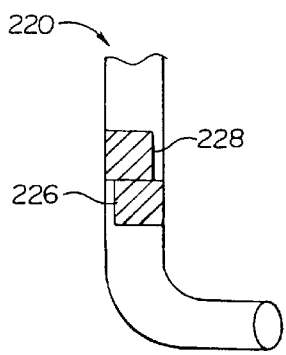
Figure 8E:
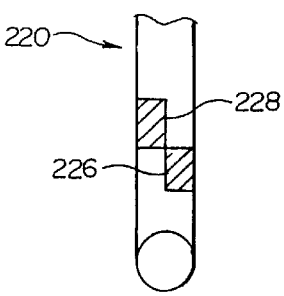
Figure 8F:
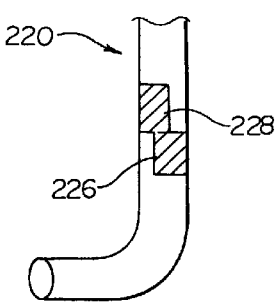
Figure 8G:
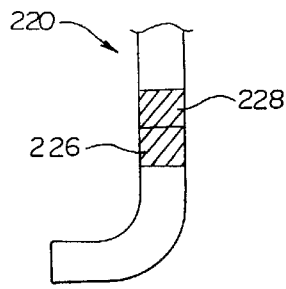
Figure 8H:
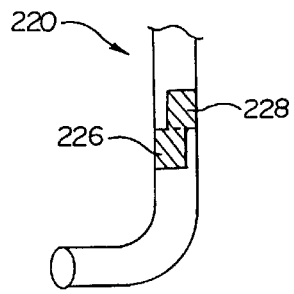

FIG. 8A illustrates a catheter shaft 220 somewhat similar to catheter shaft 200 of FIG. 7. Catheter shaft 220 has a distal end 224, a first or left marker portion 226, and a second or right marker portion 228. Together, first and second marker portions 226 and 228 form an asymmetric marker 230 which is asymmetric about a bisecting plane extending through the center longitudinal axis of catheter shaft 220. In FIG. 8A, catheter shaft 220 is rotated such that catheter distal end 224 is disposed at an angle of zero degrees (0°) relative to the viewer. Catheter shaft distal end 224 is directed directly at the viewer. FIG. 8B illustrates catheter shaft 220 rotated at a forty-five degree (45°) angle relative to the viewer, yet still remaining in a somewhat forward disposition. Similarly, FIG. 8C illustrates catheter 220 rotated at ninety degrees (90°) relative to the viewer, and FIG. 8D has the catheter pointed at a one hundred thirty five degree (135°) angle away from the viewer. FIG. 8E illustrates catheter shaft 220 being pointed directly away from the viewer, followed by FIG. 8F, which illustrates the same catheter pointing away from the viewer, but at an angle of two hundred twenty five degrees (225°). FIG. 8G illustrates catheter shaft 220 being rotated sufficiently to point two hundred seventy degrees (270°) relative to the line of view, toward the side. Finally, FIG. 8H illustrates catheter shaft 220 being pointed three hundred fifteen degrees (315°) away from its initial location, pointing mainly toward the viewer, but at a slight angle to the left.

As can be seen from inspection of FIGS. 8A through 8H, catheter marker 230 appears differently under fluoroscopy depending on the rotation of the marker relative to the viewer. In particular, the marker is asymmetrically disposed on the catheter shaft such that rotation of the catheter about its longitudinal center axis appears different, relative to a fixed viewer orthogonal to the longitudinal axis of the catheter shaft. Marker 201 thus enables a viewer using fluoroscopy to determine the angle of rotation of the catheter shaft about its longitudinal axis. This can prove useful in a myocardial revascularization procedure, where turning the catheter in varying degrees can be important, as the degree of rotation may correspond to the location of holes formed in the heart chamber wall.

Figure 9A:
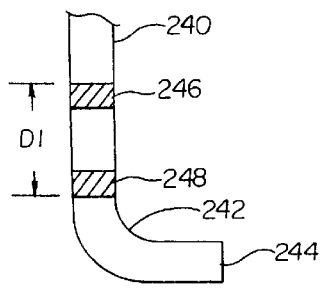
FIGS. 9A and 9B are perspective views of a guide catheter shaft including radiopaque marker bands having an inter-band distance corresponding to a desired myocardial revascularization treatment site spacing.
Figure 9B:
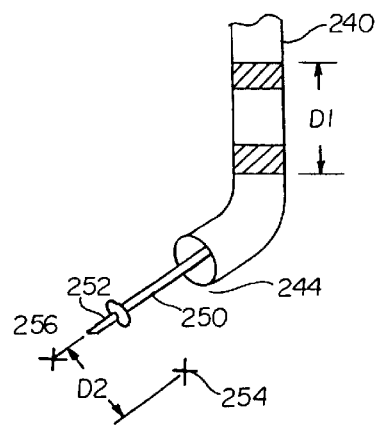

FIG. 9A illustrates a catheter shaft 240 having a bend 242 and a distal end 244. Catheter shaft 240 further has a first radiopaque marker band 246 and a second radiopaque marker band 248 disposed at a known distance "D1" apart. In a preferred embodiment, marker bands 246 and 248 are disposed at a distance apart of between about 1–2 cm. FIG. 9B illustrates catheter 240 being rotated toward and to the left of the viewer. A treatment catheter 250 may be seen to extend from catheter shaft distal end 244. Treatment catheter 250 may be seen to have a therapeutic tip 252. A first treatment site 254 is represented by an "X" in FIG. 9B. As illustrated in FIG. 9B, therapeutic tip 252 has been moved to a distance of about "D2" from first treatment site 254. In the embodiment illustrated, therapeutic tip 252 is about to treat a second site 256, where the inter-site distance, D2, is substantially equal to the D1 distance. The marker bands may thus be used as a scale to accurately space the treatments sites in the heart chamber wall. The marker bands, being spaced apart about the same distance as the desired treatment spacing, will be subject to the same magnifications and/or distortions under fluoroscopy. This means that even if the distance between the markers appears distorted under fluoroscopy, the distance between target sites will likewise be distorted by about the same amount.

Figure 10:
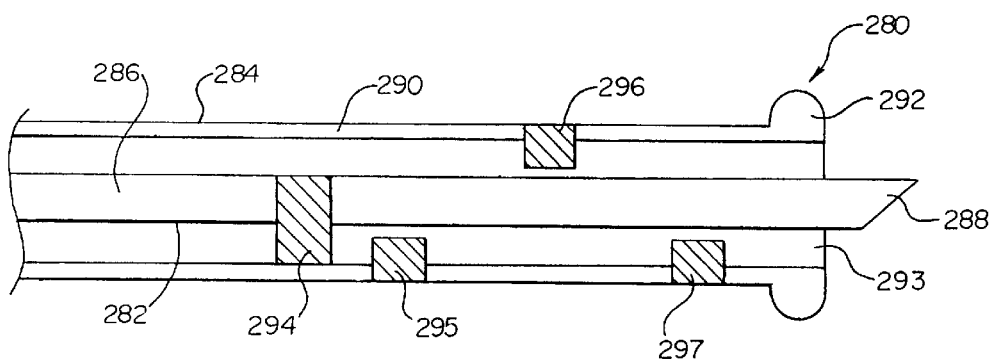
FIG. 10 is a fragmentary, longitudinal cross-sectional view of a PMR catheter having multiple stops for controlling needle penetration.

FIG. 10 illustrates a PMR catheter 280 including an inner needle 282 rotatably disposed within an outer tube 284. Inner needle 282 includes a shaft 286, and can terminate distally in a sharp needle tip 288. Outer tube 284 includes a tube wall 290, and has a distal flange or hood 292. A hole 293 is disposed within distal flange 292 for receiving needle tip 288. In the embodiment illustrated, inner needle 282 has an inner stop 294 secured to inner shaft 286. Inner stop 294 is secured to inner shaft 286 such that rotating the inner shaft rotates the inner stop. In this embodiment, outer tube 284 has outer stops 295, 296, and 297 secured at various longitudinal and angular locations along tube wall 290. As can be seen from inspection of FIG. 10, inner stop 294, if advanced further distally, will encounter outer stop 295 which will limit the distal travel of needle tip 288. It may also be seen that rotating inner shaft 286 by ninety degrees (90°) will allow inner stop 294 to clear outer stop 294 and proceed distally further. In an embodiment where inner stop 294 has a hemispherical configuration, rotating inner shaft 286 by one hundred eighty degrees (180°) would allow needle tip 288 to travel distally, yet be stopped by outer stop 296, again requiring one hundred eighty degree (180°) rotation to allow further distal travel of the needle tip. Thus, twisting the inner shaft can allow the depth of penetration to be controlled. In some embodiments, the inner and outer stops are formed of radiopaque material, allowing the degree of penetration to be observed under fluoroscopy. Having staggered stops, as illustrated in FIG. 10, allows the penetration depths to be accurately controlled from the proximal end of the catheter. This may be of particular importance in PMR procedures due to the varying thickness of the heart wall.

Figure 11A:
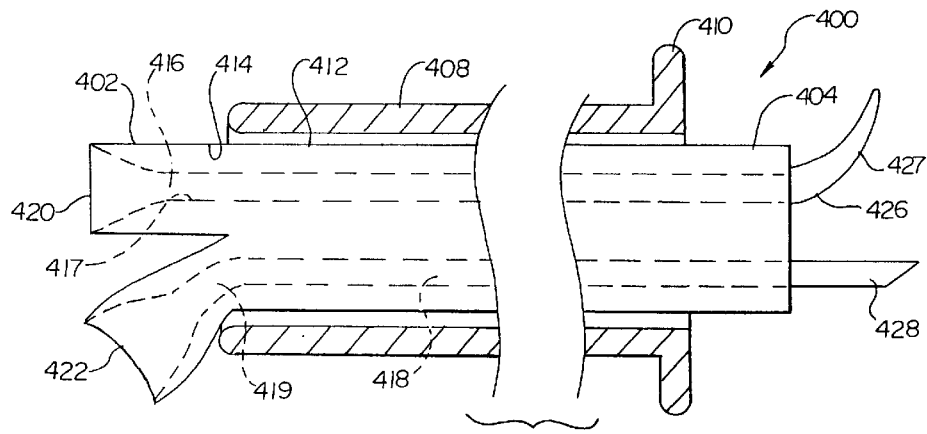
FIGS. 11A–11C are fragmentary, longitudinal cross-sectional views of a PMR catheter having side-by-side needles for injection of a drug and a radiopaque fluid.

FIG. 11A illustrates a PMR device 400 extending from a proximal region 402 to a distal region 404 and having a distal flange 410. PMR device 400 includes an outer tube 408 defining an outer lumen 412 within and slidably containing an inner tube 414 having a first lumen 416 and a second lumen 418 disposed within. In one embodiment, the two lumens are formed within a multi-lumen extrusion of inner tube 414. In another embodiment, the two lumens 416 and 418 are defined by separate tubes which are joined together along their length. First lumen 416 may have a fluid injected through a first manifold port 420 disposed in proximal region 402 extending through a first access tube 417 which can define first lumen 416 in the proximal region. First lumen 416 extends distally to a first injection needle 426 which may be seen to have an arcuate distal region 427. Similarly, second lumen 418 may be seen to extend from a second manifold port 422, through a second proximal tube 419, extending distally to a second fluid injection needle 428. In the embodiment illustrated, first injection needle 426 is curved, while second injection needle 428 is substantially straight in the distal region.

In one embodiment, first lumen 416 is used to inject radiopaque fluid, while second lumen 418 is used to inject a drug as part of the PMR procedure. In another embodiment, first lumen 416 is used to inject a drug, while second lumen 418 is used to inject a radiopaque material. In this latter embodiment, the straight needle 428 can be used to inject radiopaque material at the center of a circular pattern formed by the repeated injection of a drug through first needle 426. Injection of the radiopaque fluid allows the treating physician to visualize under fluoroscopy which areas of the heart wall have already been treated with the drug.

Figure 11B:
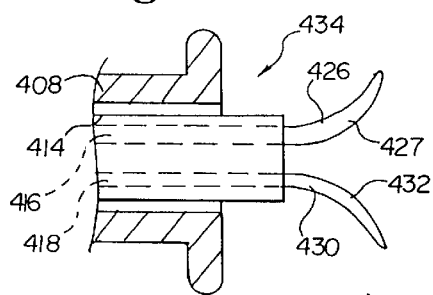
Figure 11C:
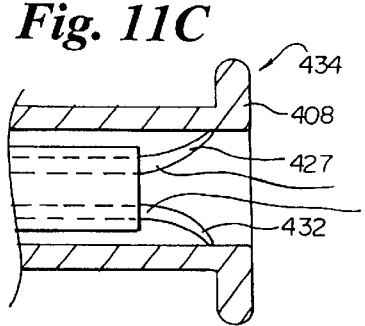

FIG. 11B illustrates a distal PMR device region 434, similar to distal region 404 of FIG. 11A, and having similar proximal regions, but having a different configuration for the two distal needles. In the embodiment illustrated, the PMR device distal region includes outer tube 408, inner tube 414, and first and second lumens 416 and 418, as in FIG. 11A. First needle 426 has arcuate region 427. In this embodiment, a second needle 430 is illustrated, also having arcuate distal segment 432. In this embodiment, both first and second needles have arcuate distal regions. FIG. 11C illustrates distal region 434 of FIG. 1B, shown in a retracted configuration. First needle 426 and second needle 430 may be seen to be retracted within outer tube 408.

Figure 12A:
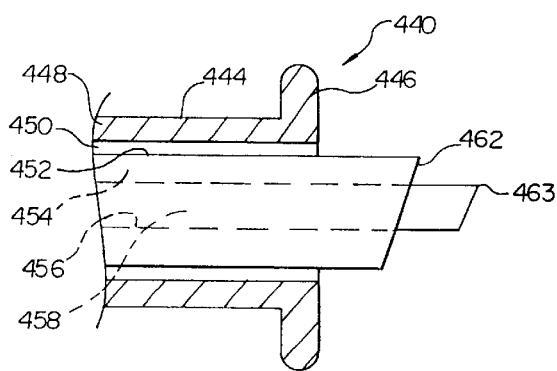
FIGS. 12A–12B are fragmentary, longitudinal cross-sectional views of PMR devices having coaxially disposed drug and dye delivery lumens.
Figure 12B:
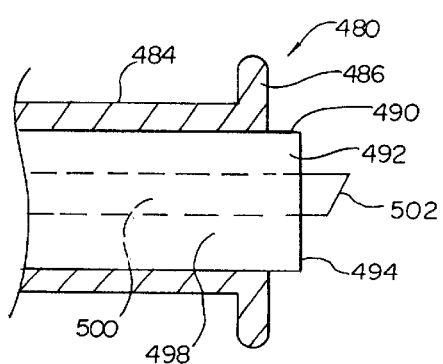

FIGS. 12A and 12B illustrate other embodiments of PMR device distal regions, with the proximal regions not requiring illustration and having somewhat similar designs to those of FIG. 11A. FIG. 12A illustrates a PMR device 440 including a distal region 444 and having a distal atraumatic flange 446. PMR device 440 includes an outer tube 448 defining an outer lumen 450 within. Outer lumen 450 includes within an intermediate or first tube 452 defining an intermediate or first lumen 454 within. Intermediate lumen 454 includes within an inner or second tube 456 defining an inner or second lumen 458 within. Intermediate lumen tube 452 extends distally and terminates in a distal injection tip 462. Second or inner tube 456 extends distally, terminating in a distal injection tip 463.

In one embodiment, first lumen 454 is used to inject a drug through needle 462. In this embodiment, second or intermediate lumen 458 is used to inject a radiopaque dye through second or intermediate needle 463. In the embodiment illustrated in FIG. 12A, intermediate tube 452 can be slidably disposed within the outer tube 444, and can have inner tube 456 slidably disposed within. In another embodiment, the functions of the first and second lumens are reversed relative to the aforementioned embodiment. In this embodiment, inner needle 463 is used to inject dye, while intermediate needle 462 is used to inject a drug. Injecting a radiopaque dye or contrast media allows the treating physician to observe which areas of the heart wall have been treated and which have not been treated, under fluoroscopy.

FIG. 12B illustrates a PMR device 480 including a distal region 484 and having a distal atraumatic flange 486. A first material may be injected through a proximal manifold port, through a first lumen 492 defined within a first or intermediate tube 490. The first material or fluid may be injected through intermediate tube 490, being injected into tissue through a first distal tip 494. A second material or fluid may be injected through a second or inner manifold port, flowing through an inner lumen 500 defined within an inner tube 498. The second media may be injected distally into tissue through a inner distal tip 502.

In the illustrated embodiment, tube 490 is fixed relative to outer tube 484, while inner tube 498 can be slidably disposed with respect to tube 490. In this embodiment, radiopaque contrast media may be injected at approximately the same site as a drug delivered in a PMR procedure. In one embodiment, a drug is injected through inner tip 502, while a contrast media is injected through tip 494. In another embodiment, contrast media is injected through tip 502, while a drug or other therapeutic substance is delivered through the outer distal tip 494. In the embodiment illustrated in FIG. 12B, outer distal tip 494 is relatively rounded at the end, with pressure being used to force material into the heart wall, rather than relying primarily on needle penetration. PMR device 480 also allows injection of contrast media near the site of drug injection. This allows the treating physician to observe the location of sites treated by PMR under fluoroscopy, distinguishing the treated sites from the untreated areas.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A myocardial revascularization preparation system comprising:
    a myocardial revascularization drug delivery catheter including an elongate tube having a lumen and a distal portion, said distal portion having an injection device in fluid communication with said lumen; and
    a drug receiving vial for receiving said catheter distal portion injection device, said vial including an inner cavity bordered at least in part by a gasket, said vial having a neck for receiving said myocardial revascularization drug delivery catheter distal portion.

2. A myocardial revascularization preparation system as in claim 1, wherein said vial cavity contains a drug neutralizing material.

3. A myocardial revascularization preparation system as in claim 2, wherein said gasket is formed of a self-sealing material.

4. A myocardial revascularization preparation system as in claim 2, wherein said vial neck includes a shoulder region for engaging said myocardial revascularization catheter distal portion.

5. A myocardial revascularization preparation system as in claim 4, wherein said myocardial revascularization catheter distal region has an expanded state and a non-expanded state, wherein said myocardial revascularization catheter distal region is sufficiently complaint to be pulled from said vial shoulder region while in said expanded state.

6. A drug neutralizing vial for preparing a drug delivery catheter, the drug delivery catheter including a distal portion having a distal injection device, the vial comprising:
    a neck for receiving said drug delivery catheter distal injection device, said vial including an inner cavity therein and a gasket for sealing said cavity and for admitting said injection device therethrough, said vial cavity containing a drug neutralizing material.

7. A drug neutralizing vial as recited in claim 6, wherein said vial neck includes a shoulder region for engaging said drug delivery catheter distal portion.

8. A drug neutralizing vial as recited in claim 6, wherein said gasket is formed of a self-sealing material.

9. A method for preparing a drug delivery catheter for use, the drug delivery catheter including an elongate tube having a lumen and a distal portion, said distal portion having an injection device in fluid communication with said lumen, the method comprising the steps of:
    providing a drug neutralizing vial for receiving said drug delivery catheter distal portion injection device, said vial including an inner cavity sealed at least in part by a gasket, said vial cavity containing a drug neutralizing material therein, said vial having a neck for receiving said drug delivery catheter distal portion;
    inserting said drug delivery injection device through said gasket;
    flushing at least some of said drug through said drug delivery injection device into said vial, such that said drug is at least partially neutralized in said cavity; and
    withdrawing said drug delivery injection device from said gasket.

10. A drug delivery catheter comprising:
    an elongate tube having a distal portion, a distal end, a tube wall, and a lumen therethrough; and
    a needle having a lumen therethrough, a proximal portion, and a distal portion, said needle distal portion including a sharp distal end, said proximal portion being wider than said distal portion and having at least one protrusion for engaging said tube wall,
    wherein said needle proximal portion engages said tube distal portion, wherein said needle distal portion extends distally beyond said tube distal end, such that said at least one needle protrusion engages said tube wall to resist pulling said needle distally away from said tube,
    wherein said tube has an inner wall surface, wherein said needle protrusion protrudes outward and engages said tube inner wall surface.

11. A drug delivery catheter as in claim 10, wherein said at least one protrusion includes a plurality of barbs for engaging said tube wall.

12. A drug delivery catheter as in claim 11, wherein said barbs are inclined distally such that moving said needle distally is more difficult than moving said needle proximally.

13. A drug delivery catheter comprising:
    an elongate tube having a distal portion, a distal end, a tube wall, and a lumen therethrough; and
    a needle having a lumen therethrough, a proximal portion, and a distal portion, said needle distal portion including a sharp distal end, said proximal portion being wider than said distal portion and having at least one protrusion for engaging said tube wall,
    wherein said needle proximal portion engages said tube distal portion, wherein said needle distal portion extends distally beyond said tube distal end, such that said at least one needle protrusion engages said tube wall to resist pulling said needle distally away from said tube,
    wherein said needle includes a flange abutting said tube distal end for limiting proximal travel of said needle relative to said tube.

14. A drug delivery catheter comprising:
    an elongate tube having a distal portion, a distal end, a tube wall, and a lumen therethrough; and
    a needle having a lumen therethrough, a proximal portion, and a distal portion, said needle distal portion including a sharp distal end, said proximal portion being wider than said distal portion and having at least one protrusion for engaging said tube wall,
    wherein said needle proximal portion engages said tube distal portion, wherein said needle distal portion extends distally beyond said tube distal end, such that said at least one needle protrusion engages said tube wall to resist pulling said needle distally away from said tube,
    wherein said tube wall distal region includes a hole therethrough for receiving a bonding material, wherein said needle is further secured to said tube by said bonding material being injected through said hole.

15. A drug delivery catheter comprising:
    an elongate tube having a distal portion, a distal end, a tube wall, and a lumen therethrough; and
    a needle having a lumen therethrough, a proximal portion, and a distal portion, said needle distal portion including a sharp distal end, said proximal portion being wider than said distal portion and having at least one protrusion for engaging said tube wall,
    wherein said needle proximal portion engages said tube distal portion, wherein said needle distal portion extends distally beyond said tube distal end, such that said at least one needle protrusion engages said tube wall to resist pulling said needle distally away from said tube,
    wherein said at least one protrusion includes at least one helical thread for engaging said tube wall.

16. A drug delivery catheter comprising:
    an elongate tube having a distal portion, a distal end, a tube wall, and a lumen therethrough; and
    a needle having a lumen therethrough, a proximal portion, and a distal portion, said needle distal portion including a sharp distal end, said proximal portion being wider than said distal portion and having at least one protrusion for engaging said tube wall,
    wherein said needle proximal portion engages said tube distal portion, wherein said needle distal portion extends distally beyond said tube distal end, such that said at least one needle protrusion engages said tube wall to resist pulling said needle distally away from said tube,
    wherein said at least one protrusion includes a plurality of threads for engaging said tube wall.

17. A drug delivery catheter comprising:
    an elongate tube having a distal portion, a distal end, a tube wall, and a lumen therethrough; and
    a needle having a lumen therethrough, a proximal portion, and a distal portion, said needle distal portion including a sharp distal end, said proximal portion being wider than said distal portion and having at least one protrusion for engaging said tube wall,
    wherein said needle proximal portion engages said tube distal portion, wherein said needle distal portion extends distally beyond said tube distal end, such that said at least one needle protrusion engages said tube wall to resist pulling said needle distally away from said tube,
    wherein said needle is disposed within said tube lumen, said needle includes a lumen therethrough, and said lumen has a proximal throat region.

18. A method for performing myocardial revascularization, the method comprising the steps of:
    providing a myocardial revascularization catheter including a distal region having at least two radiopaque markers disposed a distance apart, and having a distal therapeutic treatment tip;
    treating a first site in said myocardium using said revascularization catheter;
    moving said distal therapeutic treatment tip away from said first site by about said distance to a second site; and
    treating said second site in said myocardium.

19. A method as recited in claim 18, wherein said treating and moving steps are performed under fluoroscopy.

* * * * *

UNITED STATES PATENT AND TRADEMARK OFFICE
CERTIFICATE OF CORRECTION

PATENT NO.    : 6,616,626 B2
DATED         : September 9, 2003
INVENTOR(S)   : Justin Crank et al.

It is certified that error appears in the above-identified patent and that said Letters Patent is hereby corrected as shown below:

Column 12,
Line 12, change "complaint" to -- compliant --.

Signed and Sealed this

Twenty-fourth Day of August, 2004

JON W. DUDAS
*Director of the United States Patent and Trademark Office*